United States Patent [19]

Ohshiro

[11] Patent Number: 4,569,334
[45] Date of Patent: Feb. 11, 1986

[54] APPARATUS FOR RESTORING THE LIGHT TRANSMITTANCE OF AN IMAGE-TRANSMITTING OPTICAL FIBER BUNDLE USED IN A FIBER OPTIC ENDOSCOPE

[75] Inventor: Susumu Ohshiro, Saitama, Japan

[73] Assignee: Fuji Photo Optical Co., Ltd., Saitama, Japan

[21] Appl. No.: 381,641

[22] Filed: May 24, 1982

[30] Foreign Application Priority Data

May 22, 1981 [JP] Japan ................................ 56-77827
May 22, 1981 [JP] Japan ................................ 56-77828

[51] Int. Cl.[4] ............................................. A61B 1/06
[52] U.S. Cl. ........................................... 128/6; 362/32
[58] Field of Search ................................. 128/4–8, 128/22, 396, 397, 634; 362/10, 32, 226, 365; 350/96.24–96.28; 250/227; 378/68

[56] References Cited

U.S. PATENT DOCUMENTS 3,131,690  5/1964  Innis et al. ............................. 128/6
3,132,646  5/1964  Hett ....................................... 128/6
3,358,573 12/1967  Bihlmaier ............................ 362/10

FOREIGN PATENT DOCUMENTS 2750520  6/1980  Fed. Rep. of Germany ......... 128/6
1289025  4/1962  France .................................. 128/6
1483314  4/1967  France .................................. 128/6
2405054  6/1979  France .................................. 128/6

*Primary Examiner*—Edward M. Coven
*Assistant Examiner*—Max F. Hindenburg
*Attorney, Agent, or Firm*—Young & Thompson

[57] ABSTRACT

Fiber optic endoscopes exposed to X-ray or γ-ray irradiation suffer discoloration of the optical fiber bundles with a reduction in light transmittance. This makes observation or examination using these devices difficult or impossible. The irradiation-induced reduction in light transmittance of image-transmitting optical fiber bundles is restored by visible light radiation emitted from a light source unit which is in turn transmitted to an end of the image-transmitting optical fiber bundle by a light-transmitting mechanism.

8 Claims, 6 Drawing Figures

APPARATUS FOR RESTORING THE LIGHT TRANSMITTANCE OF AN IMAGE-TRANSMITTING OPTICAL FIBER BUNDLE USED IN A FIBER OPTIC ENDOSCOPE

BACKGROUND OF THE INVENTION

The present invention relates to an apparatus for restoring the light transmittance of an image-transmitting optical fiber bundle whose image-transmitting ability has been reduced by X-ray or γ-ray irradiation, and for thus restoring its usefulness in performing observations and examinations.

Fiber optic endoscopes in general use have two optical fiber bundles built therein, one for transmitting illumination light from the outside and the other for transmitting an image of the internal parts to be observed or examined. Each of said optical fiber bundles comprises an extremely large number of optical fibers with their opposed end portions rigidly secured together. They are free along their extent between the ends to allow the flexibility required to be inserted along a tortuous body passage. Fiber optic endoscopes which are used to observe or examine otherwise inaccessible body cavities are generally divided into two categories: medical and industrial.

In fiber optic endoscopes for medical use, upon inserting a fiber optic endoscope into a human body, a fluoroscopic observation is often taken to locate accurately an inserted position of the tip thereof relative to a region within the human body so as to ensure the safety of the person under examination. A certain fiber optic endoscope for medical use, for instance a duodenum endoscope, can be utilized for the purpose of endoscopic retrograde cholangiopancreatography (ERCP) examinations wherein a contrast medium is, in the case of a fluoroscopic observation, injected into the pancreatic and bile ducts through a tube which is inserted in a therapeutic instrument guide channel of a fiber optic endoscope. As described above, fiber optic endoscopes for medical use have many uses in connection with fluoroscopic observation. It is to be expected that fiber optic endoscopes will be used in connection with fluoroscopic observation more often in the future.

Consequently, an optical fiber bundle in a fiber optic endoscope used in connection with fluoroscopic observation is frequently exposed to irradiation in spite of its protective rubber tube which is a part of the fiber optic endoscope, which irradiation induces coloration thereof and decreases the light transmittance of the optical fiber bundle. A fiber optic endoscope having an image-transmitting fiber bundle with such irradiation-induced coloration may be unacceptable for observing or examining an image therethrough and so may be returned to the manufacturer for replacement of the image-transmitting fiber bundle. But an image-transmitting fiber bundle is very expensive; moreover, the replacement thereof is extremely complex and hence even more expensive.

We obtained empirically the result that the irradiation-induced coloration of an image-transmitting fiber bundle can be caused to fade by the application of visible light radiation, and that the light transmittance of said fiber bundle was then recovered to a degree acceptable for performing observations and examinations as described in detail in U.S. patent application Ser. No. 349,619, filed Feb. 17, 1982.

OBJECTS OF THE INVENTION

Therefore, the principal object of the present invention is to provide apparatus for easily restoring the light transmittance of an image-transmitting fiber bundle.

Another object of the present invention is to provide apparatus which is simple in construction for restoring the light transmittance of an image-transmitting fiber bundle.

SUMMARY OF THE INVENTION

The aforementioned objects of the present invention are achieved by the use of a light-transmitting means which is so arranged that one end thereof is disposed in the focal plane of a light illumination means and the opposed end is disposable adjacent to one end of an image-transmitting fiber bundle provided in a fiber optic endoscope. Visible light radiation can be transmitted from a light source to the one end of the image-transmitting fiber bundle so as to allow visible light to enter the image transmitting fiber bundle and thereby restore the image transmittance of the fiber bundle to a degree acceptable for performing examinations and observations.

BRIEF DESCRIPTION OF THE DRAWINGS

Other objects, advantages and features of novelty of the invention will be evident to those skilled in the art from a consideration of the following description, taken in conjunction with the accompanying drawings, in which.

DETAILED DESCRIPTION OF THE INVENTION

Figure 1:
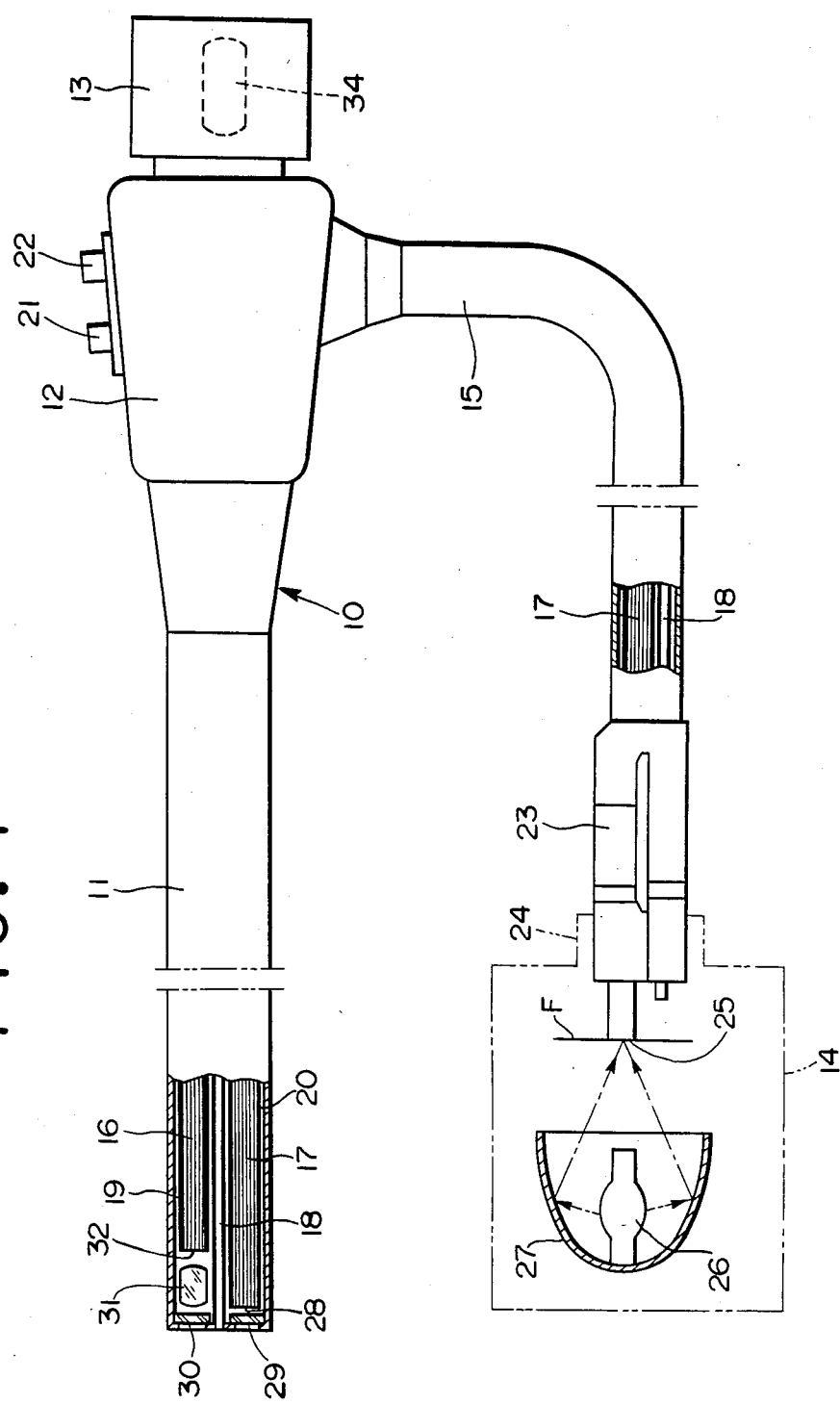
FIG. 1 is a schematic illustration of a fiber optic endoscope for medical use.

Referring now in detail to the drawings, a fiber optic endoscope 10 for medical use as illustrated in FIG. 1 comprises an elongated flexible part 11 which can be inserted into the body cavity to be examined, a remote control part 12, an ocular part 13, and an elongated extension part 15 connectible to an illumination light source device 14. The flexible part 11 has an image-transmitting fiber bundle 16 and a light-transmitting fiber bundle 17 each of which comprises an extremely large number of optical fibers each of a diameter about 10 to 20 μm, and a flexible tube 18 for feeding water and air into a human body therethrough. The ends of the optical fibers of the image-transmitting fiber bundle 16 are rigidly secured together by an adhesive such as epoxy resin so as to maintain their spatial relationship; but they are free along their extent between the ends so as to be flexible or freely movable. The light-transmitting fiber bundle 17 is constructed in the same manner as the fiber bundle 16, but it is not necessary to maintain the spatial relationship of the fibers at both ends. The fiber bundles 16 and 17 are covered by rubber protection tubes 19 and 20, respectively. The flexible part 11 is provided with a rigid distal end which is adapted to be moved to enable observation in any desired direction by operating a control knob (not shown) disposed on the remote control part 12. Operation of an air feed button 21 and a water feed button 22 cause an electromagnetic valve to operate so as to control their respective flows into cavities of a human body through the flexible tube 18.

The extension part 15 includes parts of the light-transmitting fiber bundle 17 and the flexible tube 15 extending therethrough and has a coupling means 23 provided at its distal end. The coupling means 23 can position the end face 25 of the light-transmitting fiber bundle 17 in the focal plane F of a reflecting mirror 27 which reflects visible light from a light source 26. It is desirable to employ a xenon lamp or a halogen lamp as the light source 26.

Visible light emitted from the light source 26 is partially reflected toward the incident end 25 of the light-transmitting fiber bundle 17. Visible light incident upon the incident end 25 is transmitted through the light-transmitting fiber bundle 17 and then emitted from the exit end 28 of the light-transmitting fiber bundle 17 which is disposed within the rigid distal end of the elongated flexible part 11. The visible light emitted from the exit end 28 illuminates the field to be observed through a window 29 provided with a transparent glass plate. Reflected light from the cavity surface passes through a window 30 and is made to converge by an objective 31 for observation and thereby provides an image on one end face 32 of the image-transmitting fiber bundle 16. The image formed on the end face 32 is transmitted onto the opposed end face 33 through the image-transmitting fiber bundle 16 and can be observed through an ocular assembly 34 after magnification.

The fiber optic endoscope as described above is often used in connection with a fluoroscopic observation when it is inserted into a human body. Therefore, the image-transmitting fiber bundle 16 within the elongated flexible part 11 is often exposed to irradiation, and thus gradually colored and thereby reduced in its light transmittance. As a result of this, the image-transmitting fiber bundle becomes increasingly unacceptable for observing or examining an image therethrough. The irradiation-induced reduction in light transmittance of the image-transmitting fiber bundle can be restored to a degree of light transmittance sufficient for performing observation and examination by exposing the image-transmitting fiber bundle to visible light radiation. In order to sufficiently restore light transmittance in a short time, visible light in a range of short wavelength is significantly contributive; furthermore, the use of visible light of high radiation density is more desirable.

Figure 2:
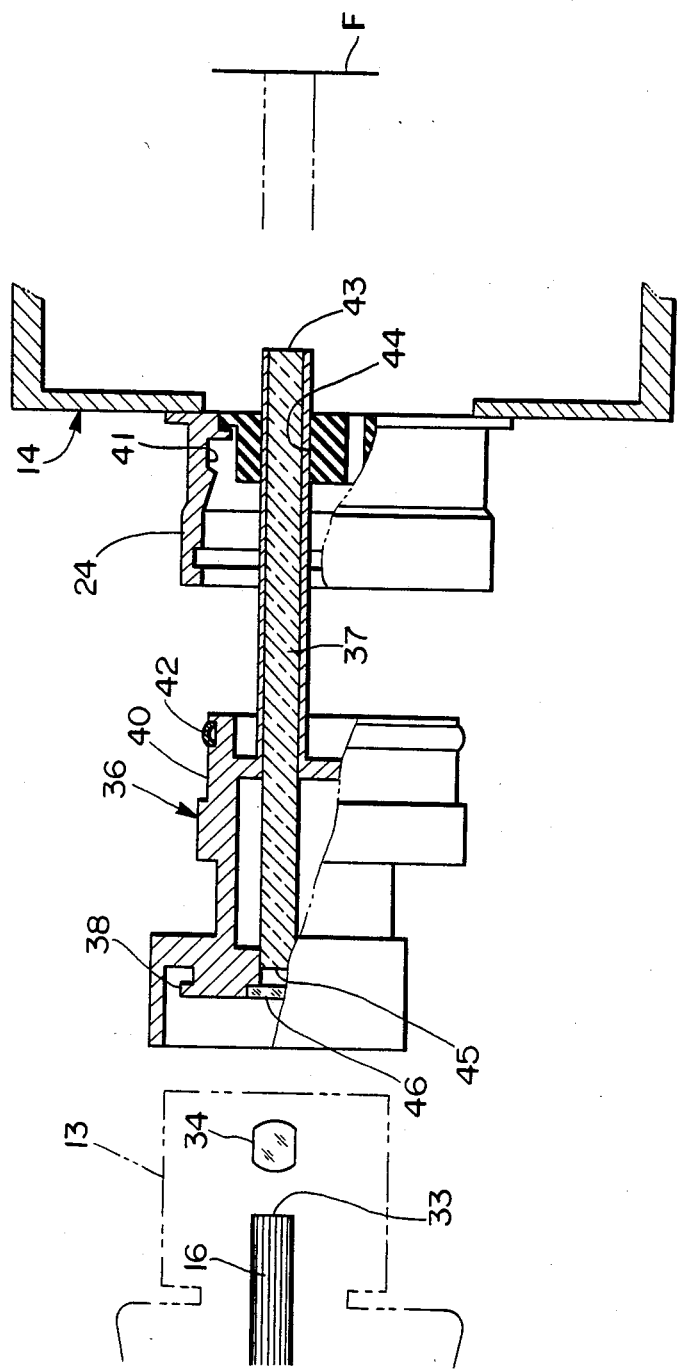
FIG. 2 is a side elevational view, partly in cross section, of an embodiment of the present invention.

FIG. 2 shows an embodiment of the present invention wherein a sleeve-like connector means is adapted to interconnect a light source device to a fiber optic endoscope through its ocular part, said light source device being usually used to produce illumination light which is transmitted through a light-transmitting fiber bundle into a cavity of the human body to be observed. The sleeve-like connector means 36 has a light-transmitting member 37 extending therethrough, a first connecting means provided at one end thereof adapted to be detachably connected to the ocular part 13 of the fiber optic endoscope, and a second connecting means provided at the other end thereof adapted to be detachably connected to the light source device 14. The first connecting means is provided with bayonet detents 38 which engage with complementary detents of a bayonet mount (not shown, but well known in the art) provided on the ocular part 13. The second connecting means is a cylindrical metal sleeve 40 which is able to smoothly fit into a socket 24 of the light source device 14 and an annular click spring means 42 which is adapted to engage in an annular groove 41 provided on the inner wall of the socket 24, thereby preventing the connector means 36 from accidentally coming out. The light-transmitting member 37 may be made of a glass rod, an optical glass fiber bundle or the like. The light-transmitting member 37 at its one end 43 projects from one end of the connector means 36 and can be inserted into a hole formed in the socket 24 into which an end of the light-transmitting fiber bundle 17 would ordinarily be inserted. The light-transmitting member 37 at its one end 43 is, when the light-transmitting means 36 is completely coupled to the light source device 14 through the second connecting means and the socket 24 as described below, located in the focal plane F thereon light emitted from the light source 26 is caused to converge (see in FIG. 1). The light-transmitting member 37 at the opposite end 45 is so arranged in the first connecting means as to closely face the ocular assembly 34 when the light-transmitting means 36 is completely coupled to the ocular part 13 through the first connecting means and the bayonet mount. Furthermore, as shown in FIG. 2, the connector means 36 is provided with a heat-absorbing filter 46 for absorbing terminal radiation contained in radiation from the light source 26. Although the heat-absorbing filter 46 is, in this embodiment, disposed in the connector means 36 so as to face the end of the light-transmitting member 37, it should be noted that the heat-absorbing filter may be located on the opposed end of the light-transmitting member 37, in the light source device 14, or in the ocular part 13.

Upon using the connector means 36 for restoring light transmittance of an image-transmitting fiber bundle in a fiber optical endoscope, the connector means 36 with its first connecting means completely coupled to the ocular part 13 through the bayonet mount is fitted into the socket 24 of the light device 14 through the second connecting means with the light-transmitting member 37 being inserted into the hole 44 until the annular click spring means 42 has engaged in the annular groove 41 on the inner wall of the socket 24. After the fitting operation as described above, the connector means 36 firmly interconnects the fiber optic endoscope 10 to the light source device 14 in such a way that the end 43 of the light-transmitting member 37 is located in the focal plane F of the light source 26 and end 45 closely faces the ocular assembly 13. Consequently, the light connector means 36, which is coupled between the light source device 14 and the fiber optic endoscope 10, can more effectively transmit light emitted from the light source 26 into the image-transmitting fiber bundle through the light-transmitting member 37 therein and the ocular assembly 34.

It is apparent from the description hereinabove that application of energy radiation to an image-transmitting fiber bundle with irradiation-induced coloration is easily performed, and thus results in the fading of the coloration and restoration of the light transmittance since the image-transmitting fiber bundle and the light source are optically coupled by the connector means interconnecting the fiber optic endoscope to the light source device.

Figure 3:
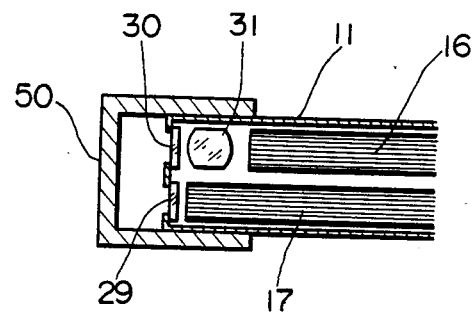
FIGS. 3 to 6 are partially sectional views of other embodiments of the present invention in which visible light radiation, passed through a light-transmitting fiber bundle disposed in a fiber optic endoscope, is deflected so as to be directed to an end surface of an image-transmitting fiber bundle.

FIG. 3 illustrates another embodiment of the present invention, in which the same numerals have been employed to denote the parts having constructions and functions similar to those of FIG. 1. Therefore, description of these parts will be omitted. The numeral 50 shows a round-bottomed cap which is so constructed as to be detachably threaded or elastically fitted onto the distal end of the elongated flexible part 11 of the fiber optic endoscope 10. It should be noted that between the distal end of the elongated flexible part 11 and the bottom wall of the cap 50 there is provided a space, and that the inner surface of the bottom wall is provided with a reflecting means so as to reflect emitted light from the light-transmitting fiber bundle toward the objective 31 located adjacent to the end of the image-transmitting fiber bundle. The reflecting means may be the bottom wall itself, with the inner surface polished or coated with a reflecting thin film.

In order to cause the fading of the irradiation-induced coloration of the fiber bundles of reduced light transmittance, the fiber optic endoscope 10 at the distal end of the elongated extension part 15 is coupled to the light source device 14 through the coupling means 23 and the socket 24, and then the light source 26 is turned on to emit illumination after the distal end of the elongated flexible part 11 is closed by the cap 50. The illumination emitted from the light source 26 is transmitted through the light-transmitting fiber bundle 17 to illuminate the inside of the cap 50 through the window 29. The illumination, after reflection by the reflecting surface of the bottom wall of the cap 50, falls upon the incident end of the image-transmitting fiber bundle 16 through the window 30 and the objective 31. As a result, the energy of the emitted light from the light source 26 is supplied to the image-transmitting fiber bundle 16 to cause the fading of the irradiation-induced coloration thereof and to thereby restore the light transmittance.

Figure 4:
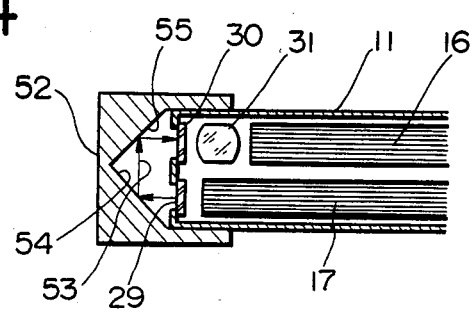

FIG. 4 shows another embodiment of the present invention, in which a modified reflecting means of the cap is illustrated as a cap 52. This cap is constructed in the same manner as the cap 50 shown in FIG. 3 with the exception of the reflecting means. The cap 52 on its inside is provided with a pair of reflecting surfaces 54 and 55 intersecting each other which serve to deflect illumination 53 from the light-transmitting fiber bundle 17 toward the image-transmitting fiber bundle 16.

In this embodiment shown in FIG. 4, the cap 52 can cause more light rays to be directed toward the image-transmitting fiber bundle 16 as compared to the case of the embodiment shown in FIG. 3.

Figure 5:
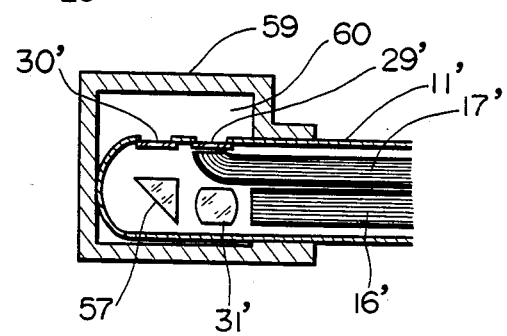
Figure 6:
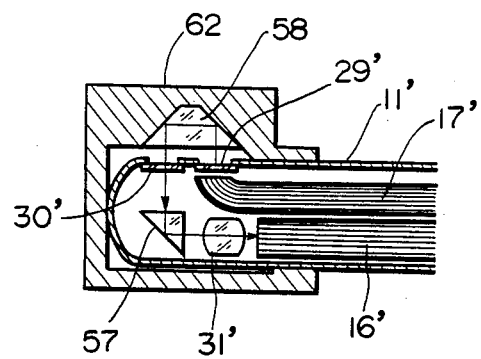

FIGS. 5 and 6 show still other embodiments of the present invention adaptable to the type of side view fiber optic endoscopes which are provided with windows 29' and 30' for illumination and observation, respectively, on one side adjacent the distal end of the elongated flexible part 11' thereof. Such fiber optic endoscopes are the same in construction as that shown in FIGS. 1 to 4, except that a prism 57 for deflecting the light path is disposed between the observation window 30' and an objective 31'.

A cap 59 shown in FIG. 5 is so constructed that the cap 59 can, when coupled to the distal end of the elongated flexible part 11', include the windows 29' and 30' therewithin and provide a space 60 therebetween. It is desirable that the inner wall of the cap 59 opposed to the windows 29' and 30' be coated with a thin reflecting film.

On the other hand, a cap 62 shown in FIG. 6 is provided with a light path deflecting prism 58 therewithin which is so arranged as to, when coupled to the distal end of the elongated flexible part 11' of the fiber optic endoscope, deflect the emitted illumination from the light-transmitting fiber bundle 17' toward the prism 57 for observation.

In order to cause fading of the irradiation-induced coloration of a fiber bundle of reduced light transmittance by using the cap 59 or 62, the cap 59 or 62 is coupled to the distal end of the elongated flexible part 11' of a fiber optic endoscope, and then the light source 26 is turned on to emit illumination. The illumination from the light source 26 is, as is well known, transmitted through the light-transmitting fiber bundle 17' to illuminate the inside of the cap 59 or 60 through the window 29'. The illumination, after being reflected by the reflecting surface of the inner wall of the cap 59 or by the deflecting prism 58 provided within the cap 62, falls upon the incident end of the image-transmitting fiber bundle 16' after passing through the observation window 30', the deflecting prism 57 and the objective 31'. As a result, energy of the emitted light from the light source 26 is supplied to the image-transmitting fiber bundle 16' to cause fading of the irradiation-induced coloration thereof and to thereby restore the light transmittance thereof.

What is claimed is:

1. A fiber optic endoscope having a light-transmitting optical fiber bundle for transmitting light to a cavity to be observed, means for illuminating an end of said light-transmitting optical fiber bundle remote from the cavity thereby to transmit light along the light-transmitting optical fiber bundle to the cavity, an image-transmitting optical fiber bundle separate from said light-transmitting optical fiber bundle and having one end adapted to receive an image from a said cavity and another end adapted to transmit an image to an ocular assembly contained in an ocular part of the endoscope, a light source unit having a light source emitting visible light radiation, light transmitting means disposed between said light source and said ocular assembly through which said light source is optically exposed to said ocular assembly for transmitting light from said light source through said light-transmitting means to said ocular assembly and thence through said image-transmitting optical fiber bundle in the reverse direction from a said image of the cavity, and means detachably connecting said ocular part to said light-transmitting means and light source unit.

2. A fiber optic endoscope as claimed in claim 1, and means detachably interconnecting said light-transmitting means and said light source unit.

3. A fiber optic endoscope as claimed in claim 2, said light-transmitting means comprising an elongated transparent member, a sleeve-like connector means supporting said transparent member and having first and second connector members, said first connector member being detachably connected to said ocular part, said second connector member being detachably connected to said light source unit.

4. A fiber optic endoscope as claimed in claim 3, in which said light source unit includes a convergent mirror for converging illumination in its focal plane, one end of said elongated transparent member being disposed in said focal plane.

5. A fiber optic endoscope as claimed in claim 4, said transparent member being a glass rod.

6. A fiber optic endoscope as claimed in claim 4, said transparent member being a bundle of glass fibers.

7. A fiber optic endoscope as claimed in claim 3, said second connector member comprising an annular click spring.

8. Apparatus as claimed in claim 3, said first connector member having bayonet detents thereon which engage with complementary detents of said ocular part.

* * * * *